(12) United States Patent
Blumenthal et al.

(10) Patent No.: US 6,814,217 B2
(45) Date of Patent: *Nov. 9, 2004

(54) METHOD AND APPARATUS UTILIZING SERVO MOTORS FOR PLACING PARTS ONTO A MOVING WEB

(75) Inventors: Jeffrey Hale Blumenthal, Batavia, OH (US); Michael Joseph Lamping, Colerain Township, OH (US); Donald Louis Wires, Loveland, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 132 days.

This patent is subject to a terminal disclaimer.

(21) Appl. No.: 10/197,023

(22) Filed: Jul. 17, 2002

(65) Prior Publication Data

US 2002/0175047 A1 Nov. 28, 2002

Related U.S. Application Data (63) Continuation-in-part of application No. PCT/US01/03188, filed on Jan. 31, 2001, and a continuation-in-part of application No. 09/620,867, filed on Jul. 21, 2000, now Pat. No. 6,450,321.
(60) Provisional application No. 60/179,895, filed on Feb. 2, 2000.

(51) Int. Cl.[7] .............................................. B65G 47/32
(52) U.S. Cl. ................. 198/459.8; 198/408; 198/460.1; 198/461.2; 198/471.1; 198/472.1; 156/520; 156/521; 156/552; 156/568
(58) Field of Search ........................ 198/471.1, 472.1, 198/803, 803.5, 408, 459.8, 460.1, 461.1, 461.2; 156/552, 567, 568, 519–521

(56) References Cited

U.S. PATENT DOCUMENTS

| | | | | |
|---|---|---|---|---|
| 4,429,781 A | * | 2/1984 | Holzhauser | |
| 5,091,039 A | * | 2/1992 | Ujimoto et al. | |
| 5,235,515 A | * | 8/1993 | Ungpiyakul et al. | |
| 5,693,165 A | * | 12/1997 | Schmitz | |
| 5,693,195 A | | 12/1997 | Saito et al. | |
| 5,776,289 A | * | 7/1998 | Steidinger | |
| 5,888,343 A | | 3/1999 | Olson | |
| 5,895,555 A | | 4/1999 | Van Den Bergh | |
| 6,022,443 A | | 2/2000 | Rajala et al. | |
| 6,086,694 A | * | 7/2000 | Winter et al. | |
| 6,149,755 A | * | 11/2000 | McNichols et al. | |
| 6,165,306 A | * | 12/2000 | Rajala | |
| 6,450,321 B1 | * | 9/2002 | Blumenthal et al. | |

* cited by examiner

Primary Examiner—Christopher P. Ellis
Assistant Examiner—Mark A. Deuble
(74) Attorney, Agent, or Firm—Michael P. Hayden; Jay A. Krebs; Ken K. Patel (57) ABSTRACT

Method and apparatus for receiving parts traveling at a first speed through a receiving zone and applying the parts onto a carrier traveling at a second speed through an application zone. Transferring devices transport the parts between the zones. The transferring devices are coupled to programmable servo motors capable of varying the speed of the transferring devices to accommodate the receiving and application processes. The receiving and application operations may be performed at matched or mismatched surface speeds. The parts to be received and applied may be formed by a rotating knife, which may vary in speed. Adhesive may be used to hold the parts on the carrier web. In some embodiments, the transferring devices transfer the parts to a bonding anvil roll and the parts and a carrier web are compressed between the bonding anvil roll and a bonding pattern roll to bond the parts to the carrier web.

20 Claims, 9 Drawing Sheets

METHOD AND APPARATUS UTILIZING SERVO MOTORS FOR PLACING PARTS ONTO A MOVING WEB

CROSS-REFERENCE TO RELATED APPLICATIONS

This application is a continuation-in-part and commonly assigned U.S. application Ser. No. 09/620,867 filed Jul. 21, 2000 now U.S. Pat. No. 6,450,321 in the name of Blumenthal et al., confirmation number 3691, and of copending and commonly assigned P.C.T. Application No. PCT/US01/03188 filed Jan. 31, 2001 in the name of Liu et al., which P.C.T. Application claims the benefit of U.S. Provisional Application No. 60/179,895 filed Feb. 2, 2000.

BACKGROUND OF THE INVENTION

The present invention relates to a method and apparatus for receiving discrete parts traveling at a speed and applying the parts to a web or other carrier traveling at a different speed.

Disposable absorbent articles, such as disposable diapers, generally have been manufactured by a process where discrete parts or components of different materials, such as leg elastic, waist elastic, tapes and other fasteners have been applied to a continuously moving carrier web. Often, the speed at which the parts are fed into the process is not the same as the speed of the carrier web itself. Thus, the speed of the parts must be changed to match the speed of the carrier web to properly apply the parts without adversely affecting the process or the finished product.

Similarly, labels are typically placed onto articles when the speed at which the labels are fed into the process is not the same as the speed of the article to be labeled. Thus, the speed of the labels must be changed to match the speed of the carrier web to properly apply the parts without adversely affecting the process or the finished product.

Several different conventional methods for changing the speed of a part or component of material such that it can be applied to a continuously moving carrier web have been known to those skilled in the art.

For example, one method has been known as the slip cut or cut & slip method. A web of material, which is traveling at a slower speed than the carrier web, is fed into a knife and anvil roll having a surface speed equal to speed of the carrier web. The material slips against the surface of the anvil roll until the knife cuts it into discrete pieces. The purpose of the slip is to ensure the correct amount of material is metered into the system at the desired tension prior to cutting. As the material is cut into the discrete parts, vacuum in the anvil roll is activated to hold the discrete part on the anvil without slipping, so that the discrete part is accelerated to the speed of the anvil roll. The anvil roll then carries the part to the point where the vacuum is released and the parts are applied to the carrier web while both the parts and the carrier web are traveling at the same speed. This method has the main drawback that the coefficient of friction between the material to be cut and the anvil roll must be low enough such that, in conjunction with the holding force keeping the materials in contact, the total tension generated in the material to be cut is not great enough to generate significant elongation in the material to be cut. This elongation, if it occurs, can contribute to high variability in the final cut length and placement of the discrete part on the carrier web.

Another method has used festoons to reduce the speed of the carrier web to match the speed of the discrete parts of material to be applied to the web. An example of this method is described in U.S. Pat. No. 5,693,165 issued to Schmitz. The carrier web is temporarily slowed down to the speed of the parts with the excess portion of the carrier web gathering in festoons. The parts of material are then applied to the carrier web while both the parts and the web are traveling at the same speed. The festoons are then released allowing the moving web to return to its original speed. This method has two main drawbacks. First, the carrier web must be festooned and then released; this may damage or otherwise change the properties of the carrier web. Second, the storage system requires a large amount of space in typical disposables production systems because there is a direct relationship between line speed and storage space needed.

Another method has utilized a cam actuated follower arm. The cam actuated follower comprises a cam follower at one end of the arm and a holding plate at the other end of the arm. The cam follower remains in contact with a fixed cam which is mounted concentric with the instantaneous center of rotation of the holding plate. As the holding plate rotates, its radial distance from the center of rotation is increased and decreased to change the surface speed of the holding plate. The discrete parts of material are placed on the holding plate when it is at its smallest radius so that the speeds match. The plate then extends radially enough during the rotation to match the speed of the plate to the speed of the carrier web. At this point the discrete parts are transferred to the carrier web. This method has two main drawbacks. First, the plate is designed to match the curvature of one radius, not both. This means that either the pick-up of the discrete part or the transfer of the discrete part, or both, will occur across a gap for some part of the transfer. This can lead to a loss of control of the discrete part, which impacts handling of parts under tension, such as leg elastics. Second, to achieve the desired change in speed, the mechanical elements typically used, such as cams or linkages, become fairly large to stay within acceptable design limits for accelerations and rise angles. This size leads to increased cost and reduced flexibility, as the unit must be redesigned for each application.

Another method has utilized noncircular gears to change the speed of a transferring device. The means rotates at a constant radius, but the rotational velocity is varied between a minimum and a maximum to pick up the discrete part at its speed and place the part on the carrier web at its speed. This eliminates the size issues and speed or gap mismatch issues, but relies on mechanical means to achieve the change in rotational velocity. The drawback of this is that new transmission parts (gears or other means) are required each time a change in product design occurs that changes placement pitch length, discrete part length, or other key factors. This can be expensive and time-consuming to change. An example of this method is described in U.S. Pat. No. 6,022,443 issued to Rajala and Makovec.

BRIEF SUMMARY OF THE INVENTION

In response to the discussed difficulties and problems encountered in the prior art, a new method and apparatus for receiving discrete parts traveling at a speed, changing the speed of the parts to match the speed of a carrier web or body, and applying the parts to the carrier has been discovered.

In one aspect, the present invention concerns an apparatus for receiving discrete parts traveling at a first speed and applying the parts to a carrier traveling at a second speed. The apparatus comprises at least two rotatable transferring devices and an independent driving mechanism for each transferring device. Each rotatable transferring device comprises at least one shell segment configured to move along an orbital path through a receiving zone where the parts are received and an application zone where the parts are applied to the carrier. The carrier might comprise a continuous moving substrate web or might be another apparatus such as a roll or drum. The driving mechanism utilizes a programmable motor such as a servo motor to transmit rotational energy to the rotatable transferring device. The driving mechanism may transmit rotational energy to the rotatable transferring device through a direct connection or a transmission interposed therebetween. The transmission may include gear to gear contact or gearboxes.

As compared to conventional methods, such as the cut & slip method described above, for changing the speed of a discrete part so that it can be applied to a carrier, utilizing a programmable motor provides the ability to obtain greater changes in speed, to maintain constant speeds for a fixed duration, and to simplify the set-up process when changing from one product to another. Thus, the use of programmable motors can provide a more precise control of the length and placement of the part onto the carrier while offering great flexibility in the type of parts that are to be made.

BRIEF DESCRIPTION OF THE DRAWINGS

The present invention will be more fully understood and further advantages will become apparent when reference is made to the following detailed description of the invention and the accompanying figures. The figures are merely representative and are not intended to limit the scope of the appended claims.

FIG. 9b is a side view of the apparatus shown in FIG. 9a.

DETAILED DESCRIPTION OF THE INVENTION

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teaches or discloses the present invention.

The present invention provides a method and apparatus for receiving discrete parts traveling at a first speed and applying the parts to a carrier traveling at a second speed. The apparatus and method are particularly useful for applying any part to a carrier useful in the making of disposable absorbent articles or for placing labels onto articles. It is readily apparent, however, that the method and apparatus would be suitable for applying any part to a substrate web or carrier of parts.

Figure 1:
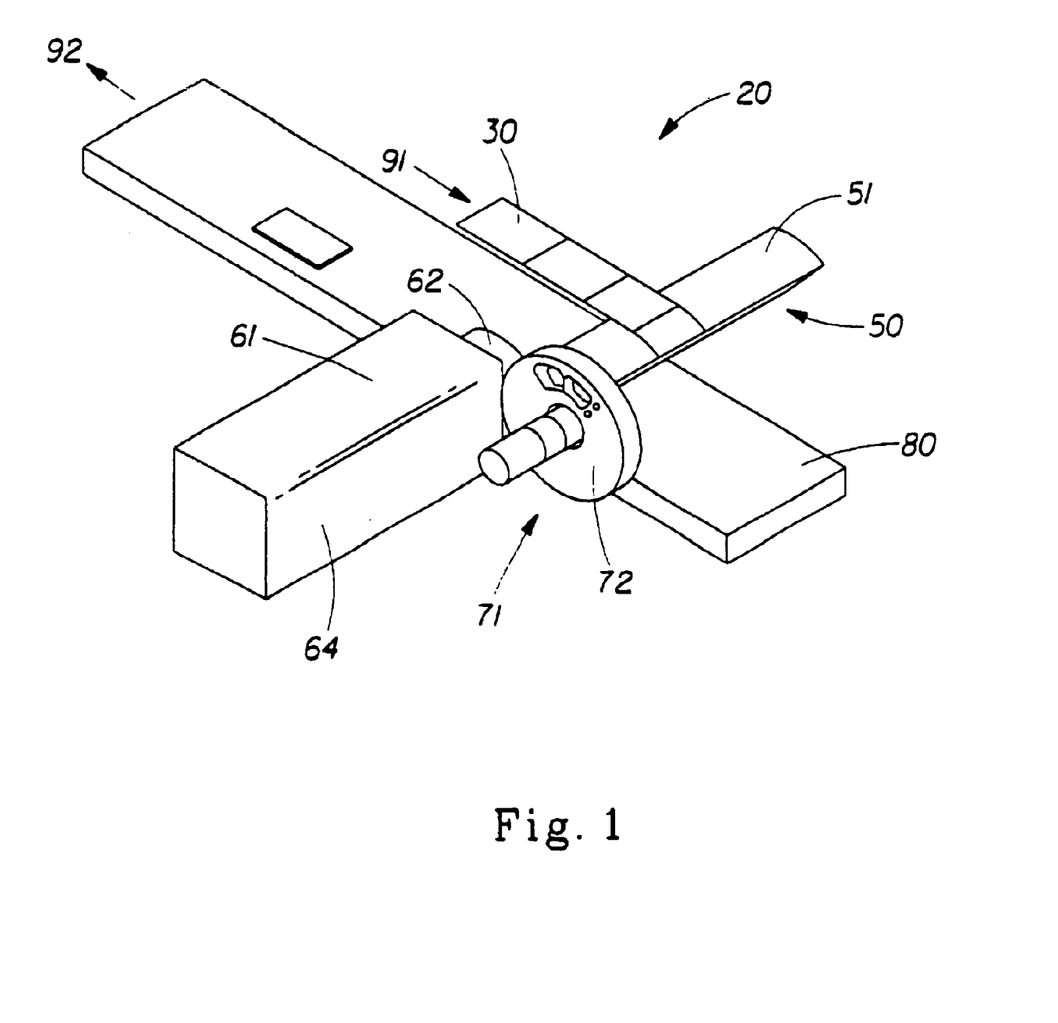
FIG. 1 representatively shows an isometric view of one example of an apparatus of the present invention.
Figure 2:
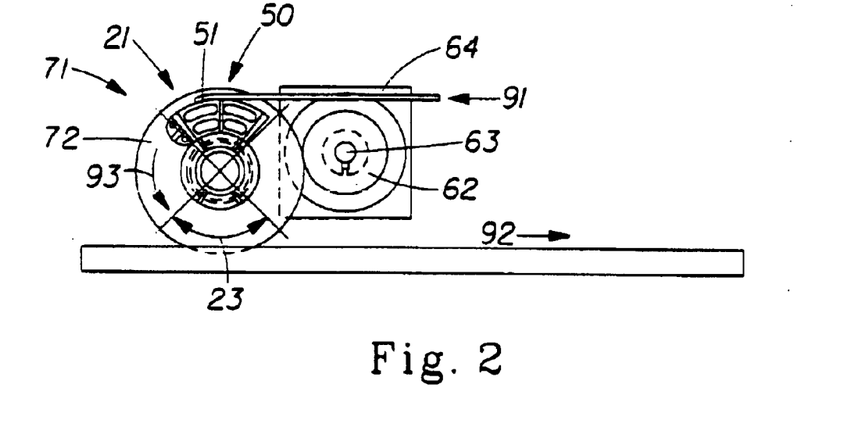
FIG. 2 representatively shows a schematic side view of the apparatus in FIG. 1.

Referring now to FIGS. 1 and 2, there is representatively shown an aspect of the invention wherein an apparatus generally indicated at 20 receives discrete parts 30 traveling at a first speed in the direction indicated by the arrow 91 associated therewith and applies the parts 30 to a carrier 80 traveling at a second speed in the direction indicated by the arrow 92 associated therewith. The illustrated example of the apparatus 20, as representatively shown in FIGS. 1 and 2, further comprises a driving mechanism 61 for transmitting rotational energy to a driven mechanism 71. The driving mechanism 61 includes a connection to the driven mechanism using any technique known to those skilled in the art such as, for example, gear to gear connection, transmission belting and pulleys, gearboxes, direct couplings, and the like or any combinations thereof. For example, in FIG. 1 the driving mechanism is connected to a driving gear 62 which transmits rotational energy to a driven gear 72 connected to the driven mechanism 71. In use, the driving gear 62 engages and rotates the driven gear 72 which, in turn, rotates the transferring device 50.

The illustrated example of the transferring device 50 comprises at least one shell segment 51 connected to the driven mechanism 71. The shell segment 51 of the transferring device 50 can be connected to the driven mechanism 71 by any technique known to those skilled in the art such as, for example, bolts, screws, pins, keys and matching keyways, connector parts such as shafting or brackets, welding and the like or combinations thereof. For instance, the shell segment 51 shown in FIG. 1 is connected directly to the driven gear 72 by fitting the end of the shell segment 51 into a mating hole in the driven gear 72 and locking it into position with a pin. Similarly, other components of the apparatus 20 can be connected together employing the above described assembly techniques.

The dimensions of the shell segment 51 may vary depending upon the desired output of the apparatus 20 and the size and shape of the discrete articles 30 being transferred. The shell segment 51 may comprise a crescent-shaped member having an outer, peripheral arc length spanning from about 5 degrees to about 340 degrees, an outer radius ranging from about 25 mm to about 500 mm, and a width ranging from about 50 mm to about 750 mm. As the driven mechanism 71 rotates, the transferring device 50 travels in the direction indicated by the arrow 93 as shown in FIG. 2. The circumferential, outer peripheral surface of the shell segment 51 defined by am outer radius, travels along and defines an orbital path that passes through a receiving zone 21 and an application zone 23. The receiving zone 21 and the application zone 23 are defined by the respective regions of the orbital path traveled by the shell segment 51.

The illustrated example of the driving mechanism 61 includes a rotatable circular driving gear 62 connected to an input shaft 63. In this example, the input shaft 63 is the output shaft of the motor 64. The driven mechanism 71 is placed parallel to the driving mechanism 61 such that the driving gear 62 meshes with the driven gear 72 using gear set-ups known to those skilled in the art. In use, the motor 64 rotates the input shaft 63 which rotates the driving gear 62 which, in turn, rotates the driven gear 72 and transferring device 50.

Alternatively, the driven mechanism 71 may include any mechanism known to those skilled in the art by which rotational energy can be conducted from one shaft to another such as, for example, v-belts, timing belts, continuous chains and the like or combinations thereof. Further, the driven mechanism 71 may include any mechanism known to those skilled in the art by which input velocity can be variably modified to an output source such as, for example, cams, linkages, and the like or combinations thereof as long as the changes in rotational speed are substantially created by the motor 64.

It will be further appreciated that the method and apparatus 20 of the invention can utilize one or, in the alternative, two, three or more combinations of transferring devices 50, driven mechanism 71, driving mechanism 61 and motor 64 in series to achieve the desired application of the discrete parts to the carrier. The different combinations may allow the use of a continuously moving web to supply the discrete parts. In addition, greater speed ratio differentials may be achieved by using combinations of transferring devices, driven mechanisms, driving mechanisms and motors in series.

Figure 3:
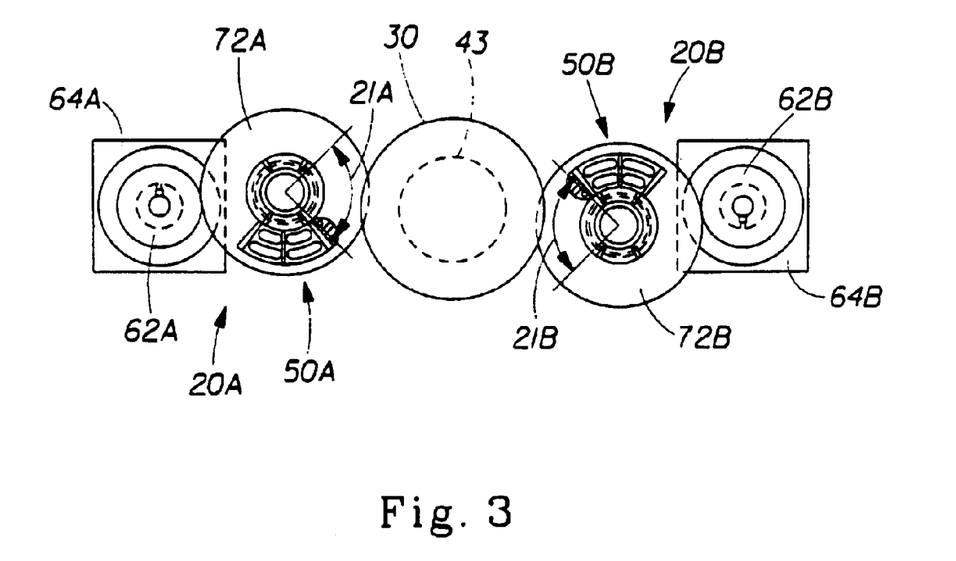
FIG. 3 representatively shows a schematic side view of the apparatus used in the present invention arranged in series.

It will be further appreciated that the method and apparatus 20 of the invention, when used in series, do not need to operate at the same receiving zone 21 and application zone 23. For example, referring to FIG. 3, there is representatively shown one apparatus 20A comprising one transferring device 50A connected to a motor 64A by a driving gear 62A and driven gear 72A and a second apparatus 20B comprising one transferring device 50B connected to a motor 64B by a driving gear 62B and a driven gear 72B. Apparatus 20A uses receiving zone 21A to accept parts 30 from a drum 43 while apparatus 20B uses receiving zone 21B to accept parts 30 from the same drum 43 at a different rotational position on said drum.

Figure 4:
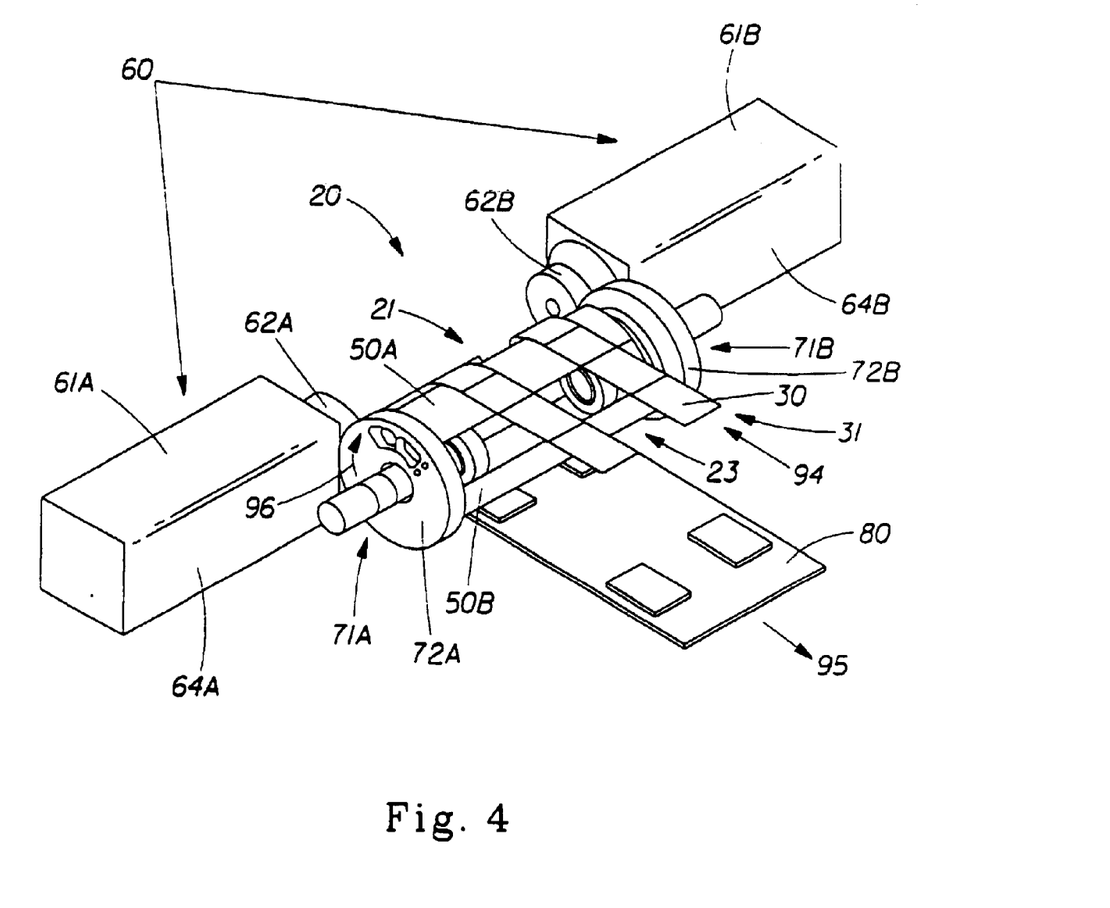
FIG. 4 representatively shows a perspective view of an apparatus according to the present invention comprising two transferring devices.

Another aspect of the invention shown in FIG. 4 comprises an apparatus 20 receiving discrete parts 30 of a web of an material 31 traveling at a first speed in the direction indicated by the arrow 94 associated therewith and applies the parts 30 to a carrier 80 traveling at a second speed in the direction indicated by the arrow 95 associated therewith. The illustrated example of the apparatus 20 comprises two rotatable transferring devices, represented by 50A and 50B, for receiving and applying the parts 30. The apparatus 20 further comprises a driving system 60 having two driving mechanisms 61A and 61B, each of which includes a motor 64A, 64B and a driving gear 62A, 62B for transmitting rotational energy to the driven mechanism 71A, 71B represented by the driven gear 72A, 72B.

As illustrated in FIG. 4, each transferring device 50A and 50B comprises a shell segment 51A, 51B connected to a driven gear 72A, 72B. As each gear rotates, the transferring devices 50A, 50B travel in the direction indicated by the arrow 96 associated therewith. In use, the circumferential, outer peripheral surface of the shell segments 51A, 51B travels along and defines an orbital path that passes through a receiving zone 21 and an application zone 23 defined by the respective regions of the orbital path traveled by the shell segments 51A, 51B of transferring devices 50A and 50B.

The size and shape of the shell segments 51A and 51B may vary as the number of shell segments per transferring device changes. For example, if the apparatus includes two transferring devices as representatively illustrated in FIG. 4, each shell segment 51A and 51B may have an outer peripheral arc length which spans from about 5 to about 175 degrees of the orbital path of the transferring devices 50A and 50B.

Each driven mechanism 71A, 71B may include any mechanism known to those skilled in the art by which rotational energy can be conducted from one shaft to another such as, for example, v-belts, timing belts, continuous chains and the like or combinations thereof. Further, the driven mechanisms 71A, 71B may include any mechanism known to those skilled in the art by which input velocity can be variably modified to an output source such as, for example, cams, linkages, and the like or combinations thereof as long as the changes in rotational speed are substantially created by the motor 64. Alternatively, a first driven mechanism may connect to a first transferring device using a first shaft from a driven gear, and a second driven mechanism may be connected to a second transferring device using concentric shafting around the first shaft.

Figure 5:
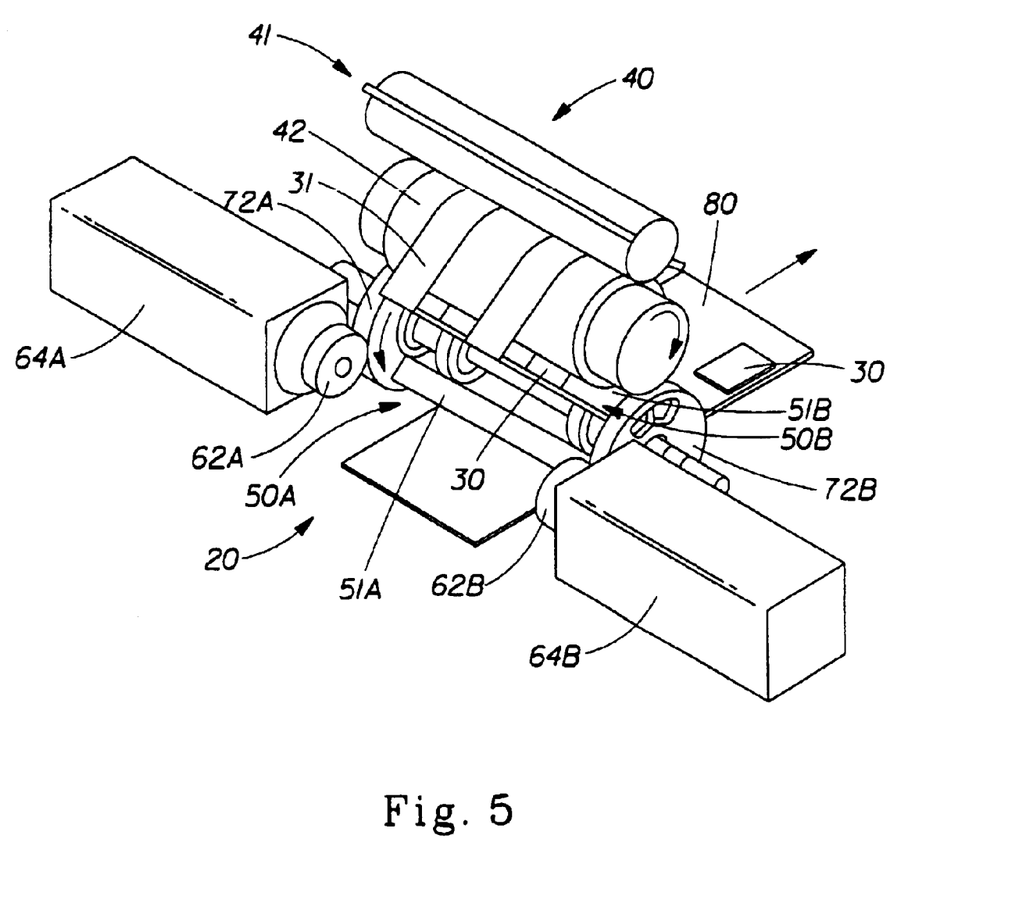
FIG. 5 representatively shows a perspective view of the apparatus shown in FIG. 4 including a cutting device.

The apparatus 20 may further comprise a cutting device 40 comprising, as representatively illustrated in FIG. 5, a knife roll 41 and a knife anvil roll 42 to sever the continuously moving web of material 31 into discrete parts 30 prior to or concurrent with the transfer of the discrete parts to the shell segments 51A, 51B of the transferring devices 50A, 50B. In certain aspects of the invention, the knife anvil roll 42 may be omitted and the knife roll 41 can be made to sever the web as it is held on the shell segment of the transferring device. The cutting device 40 may comprise a rotary cutter as shown or any other mechanism known to those skilled in the art capable of severing a web of material into discrete parts. For example, the cutting device may comprise any known form of a rotary cutter, such as a pinch knife, a die roll, etc. or may comprise a non-rotary cutter, such as a reciprocating knife, a hot wire cutter, a laser, etc.

The cutting device may be driven by an independent driving mechanism incorporating a programmable motor using a specific control routine or configuration that includes a set of preprogrammed or operator defined control steps or set points. As is known in the art, the control steps or configuration may, for example, include instructions on the velocity and/or position of the motor relative to a master reference signal, to another portion of the apparatus, or to a product. The programmable motor may vary the speed to ramp the cutting device up and down to predefined speed set points. For example, a cutting device may be driven at such a rate that its cutting surface moves at one surface speed while severing the web of parts material into discrete parts and at another surface speed during intervals between the intermittent severing of the parts from the web. Such a variable cutting speed profile may be useful, for example, in situations in which matched speed cutting of various lengths of parts from the web is desired, because a cutting device having a fixed pitch can be used without modification for different part lengths by reprogramming the cutting speed set points.

Alternately, the continuously moving web of material may be placed directly on the shell segments of multiple transferring devices so that the web lies on multiple segments at once allowing for the planned acceleration of one device to generate a force necessary to sever a single part from the web. Such severing may be facilitated by perforating the web upstream of the receiving zone so that the parts break at a desired perforation during acceleration.

For receiving the parts in the receiving zone, the transferring device, as representatively illustrated in the various configurations of the invention, may further include a gripping mechanism so that the outer concave surface of the shell segment can capture a part in the receiving zone and transport the part to the application zone. For this embodiment, the gripping mechanism may include a vacuum that can be selectively imposed through ports in the shell segment leading to the outer concave surface. For instance, the vacuum may be activated in the receiving zone to seize the parts and deactivated in the application zone to release the parts to the carrier. In this manner, positive control is maintained over the parts at all times during the transfer process. Alternatively, the gripping mechanism may include any technique known to those skilled in the art for gripping and releasing parts such as, mechanical clamps, electrical clamps, magnetic clamps and the like or combinations thereof.

Figure 11:
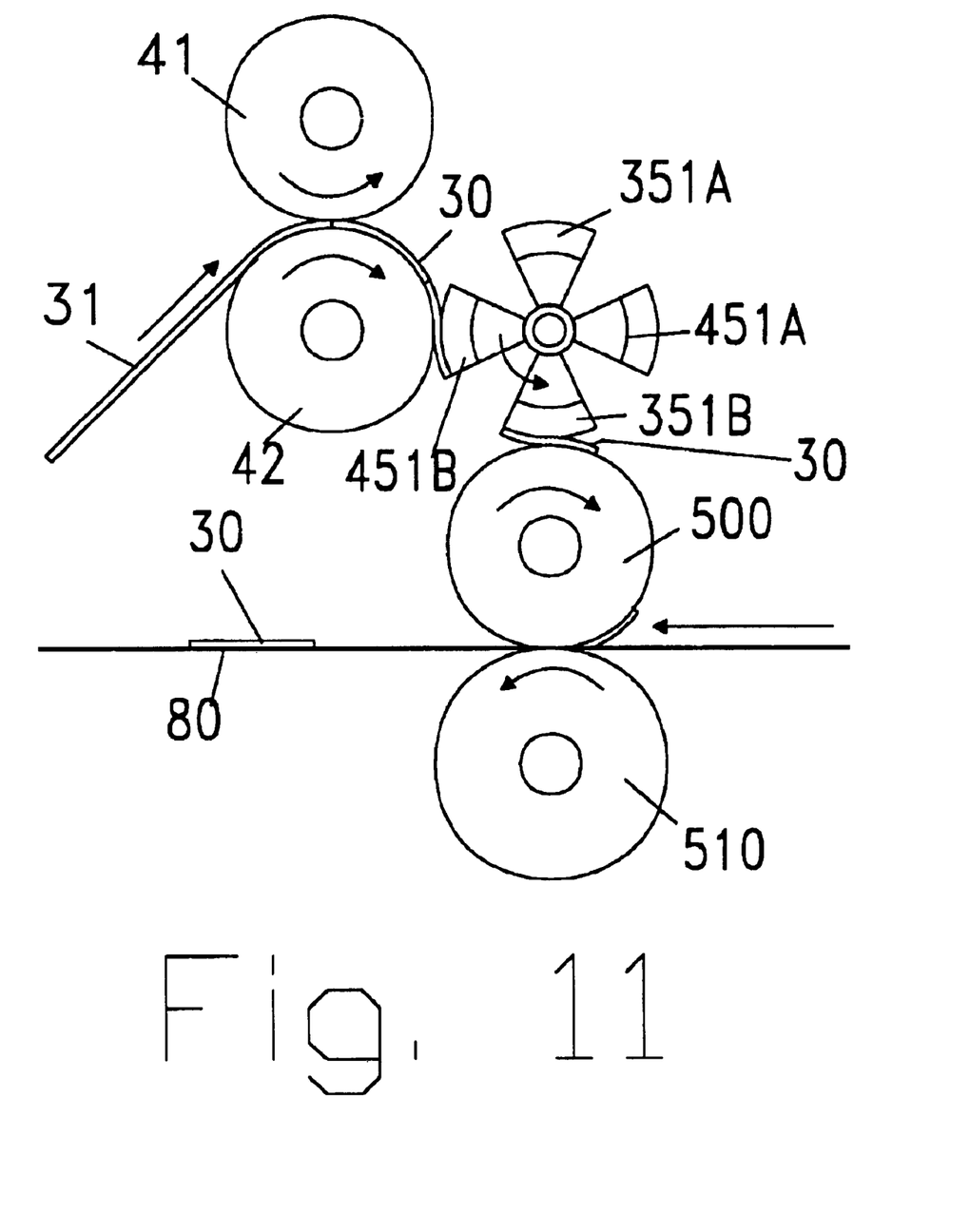
FIG. 11 shows an embodiment including a bonding anvil roll and a bonding pattern roll.

For transferring the parts to the carrier in the application zone, the apparatus may comprise any of a variety of options known to those skilled in the art such as, adhesive applied on the part, adhesive applied on the carrier, electrostatic charge between the part and carrier, vacuum on the carrier and the like or combinations thereof. Alternately, the transfer can include the generation of a weld between the part and the carrier by any of a variety of means known to those skilled in the art, such as pressure generation at a nip formed between the shell segment and an opposing roll at transfer, interaction between a pattern on the shell segment and an ultrasonic horn behind the carrier at transfer, and the like, or combinations thereof. In some embodiments, compression of the parts and a carrier web between a bonding pattern roll and a bonding anvil roll may be used to generate a weld and thereby bond the parts to the carrier web. For example, FIG. 11 shows an embodiment in which two independently driven transferring devices receive parts from knife anvil roll 42 and transfer the parts to bonding anvil roll 500, instead of applying them directly onto carrier web 80, after which the bonding anvil roll carries the parts around to the application zone, where the parts and the carrier web are compressed between the bonding anvil roll 500 and the bonding pattern roll 510 to bond the parts to the carrier web.

In addition, in order to aid the welding process, the part may be modified on the shell segment by energy addition using any mechanism known to those skilled in the art such as, for example, hot air currents, ultraviolet lighting, laser bombardment and the like or combinations thereof.

The use of a programmable motor in the apparatus, as representatively illustrated in the various aspects of the invention described above, provides an inexpensive and adaptable method for receiving parts 30 traveling at a speed and applying the parts to a carrier 80 traveling at a different speed. The variable angular velocity is produced by varying the current supplied to the motor. Since the driven mechanism is coupled to the output of the motor, changes in the angular velocity and position of the motor directly correlate to changes in the angular velocity and position of the transferring device. The current supplied to the motor can be controlled using any of a variety of a methods for programming motors known to those skilled in the art such as, standard cam curve functions, a reference data table containing reference points, desired motor encoder points, and the like or combinations thereof.

Figure 6:
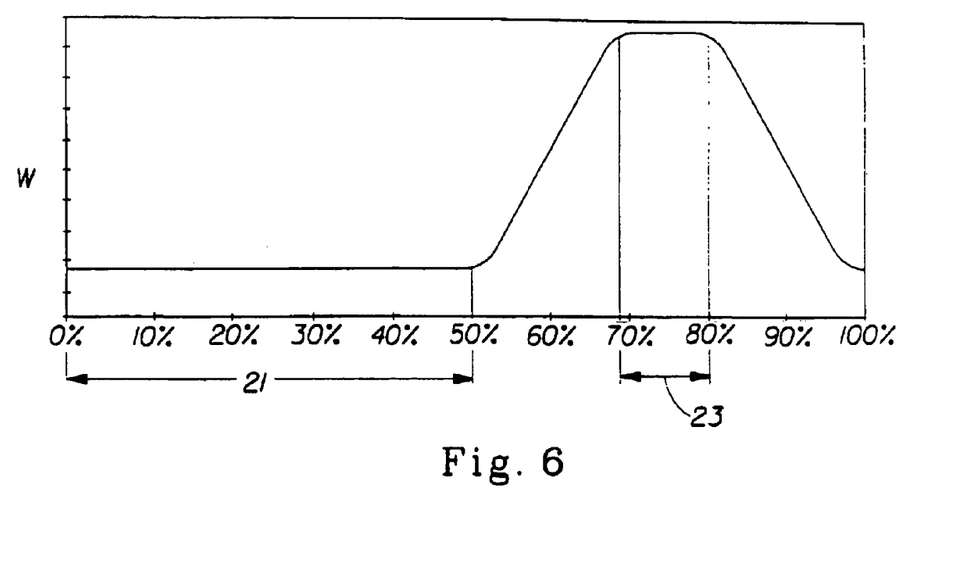
FIG. 6 representatively shows a speed profile for a typical motor output.
Figure 7:
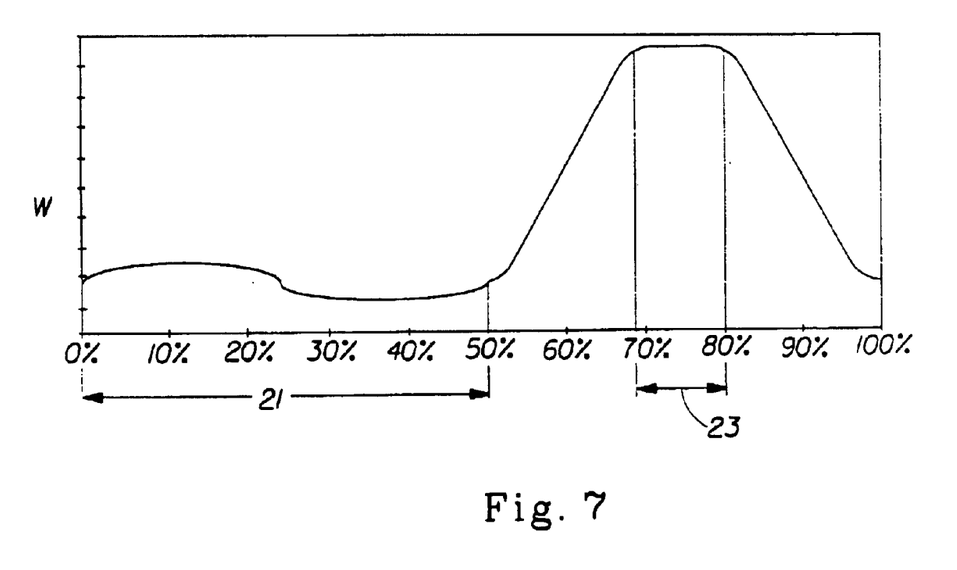
FIG. 7 representatively shows an alternate speed profile for a motor output wherein one of the fixed speed regions has been changed to variable speed.

The speed profile of a typical motor setting is representatively illustrated in FIG. 6. As shown, the programmable motor 64 used to drive the transferring device 50 of the present invention can provide variable angular velocities including periods where the velocity remains constant for a fixed duration. These constant velocity dwell times can be advantageous in the receiving zone 21 and the application zone 23 particularly when the pick up and transfer occurs over substantial arc lengths of contact. Alternatively, one or more of the constant speed regions can be changed to a controlled variable speed region as representatively illustrated in FIG. 7. This would enable the part 30 to be picked up in the receiving zone 21 at a variable speed, which, when the part 30 is elastic, would allow tensions to be varied incrementally therein which may be desirous in certain product features. In another example, the constant speed of the motor 64 in the application zone 23 can be such that the corresponding speed of the transferring device is different from speed of the carrier at transfer. Such speed variations generate tension in the part 30 by incrementally transferring the part 30 in a controlled manner from one means traveling at one surface speed to a second means traveling at a second surface speed.

It will be further appreciated that the velocity of the transferring device 50 outside of the application zone or the receiving zone can be tailored to aid the performance of secondary processes including adhesive application, printing of identification or registration marks, application of bonding aids, moisture addition and the like and combinations thereof. Such changes in velocity may be beneficial by presenting specific velocity profiles or even additional periods of constant velocity, which would allow for more precise interaction with the secondary processes being performed.

Programmable motors, such as those used in the present invention, can be purchased from any number of suppliers of programmable motors such as Rockwell Automation, located in Milwaukee, Wis. Further, the program inputs to the motors can be generated by one of ordinary skill in the art if provided with the analytical representation of the desired output function as representatively illustrated in FIG. 6. For instance, the creation of the electronic cam profile for the motor can be developed by first determining the key input variables. The key input variables are based on desired product features, the base design of the apparatus 20 and the desired cycle speed of the apparatus 20. Secondly, the radius of the outer surface of the transferring device 50 is determined. Once the radius is determined, the required cam inputs of rotational velocities, distances traveled and time available for acceleration can be calculated, which serve as the input to the cam profile generator. For example, in a system with the following inputs:

N=the number of transferring devices 71 used in the apparatus 20

H=the number of shell segments 51 per transferring device 71

$L_{s,part}$=distance from lead edge of first part 30 received in a given transfer to transferring device 50 to lead edge of part 30 received in the next cycle of transfer to a transferring device 50 in the apparatus 20

$L_{s,product}$=distance from lead edge of first product zone on carrier 80 to which parts 30 are applied in a given transfer from transferring device 50 to lead edge of product zone on carrier 80 to which parts 30 are applied in the next cycle of transfer from a transferring device 50 in the apparatus 20

$V_{min}$=average surface speed of the shell 51 on the transferring device 50 in receiving zone 21

$V_{max}$=average surface speed of the shell 51 on the transferring device 50 in application zone 23

$\tau$=cycle time of a given lane of product making $\tau_R$=time in receiving zone 21, typically of value $\tau$ when $V_{min}$=incoming speed of parts 30

$\tau_A$=time in application zone 23, typically of value Ratio*$\tau$ when $V_{max}$=speed of carrier 80

The following dependent variables can be computed:

Ratio=$L_{s,part}/L_{s,product}$

Radius=distance from effective center of rotation of transferring device 50 to outer surface of shell 51 on transferring device 50

$\tau_{TRANS}$=time in transition from $V_{min}$ to $V_{max}$=N*$\tau$−$\tau_R$−$\tau_A$=(N−1−Ratio)*$\tau$ $\omega_{min}$=average angular velocity of transferring device 50 in receiving zone 21=$V_{min}$/Radius $\omega_{max}$=average angular velocity of transferring device 50 in application zone 23=$V_{max}$/Radius $\theta_{min}=\omega_{min}*\tau_R=\omega_{min}*\tau$ $\theta_{max}=\omega_{max}*\tau_A=\omega_{max}*$Ratio*$\tau$ $\theta_{transition}=2*\pi/H-\theta_{min}-\theta_{max}=2*\pi/H-\omega_{min}*\tau-\omega_{max}*$Ratio*$\tau$ The Radius may be determined by assuming that the average angular velocity, $\omega_{ave}$, of the transferring device 50 during the transition from the receiving zone 21 to the application zone 23 is equal to $(\omega_{min}+\omega_{max})/2$. This means that the distance traveled during the transition $\theta_{transition}=\omega_{ave}*\tau_{TRANS}$. However, $\theta_{transition}$ must also be equal to $2*\pi/H-\theta_{min}-\theta_{max}$. Consequently, by setting the two equations for $\theta_{transition}$ equal to one another the following expression for Radius is defined.

Radius=$(L_{s,part}*(N+1-$Ratio$)+L_{s,product}*(N-1+$Ratio$))*H/(4*n)$

Now, given the inputs, one of ordinary skill can determine $\tau_{TRANS}$, $\omega_{min}$, $\omega_{max}$, $\omega_{min}$, $\omega_{max}$ and $\theta_{transition}$ which are typical inputs needed for electric cam software programs. The generic cam programs would then create the input table for the motor 64. Note that the Radius is an optimal radius, and not the only possible radius for the set of inputs. The Radius is optimal because it uses the entire transition time for changing the angular velocity of the transferring device 50. By changing the Radius, the actual amount of time required to change speed must change or else the combined conditions of change in angular velocity and change in angular acceleration will not be met. The amount by which the Radius can be changed from optimal depends upon the torque requirements of the system under the new accelerations at the given speed and the capability of the selected motor 64.

Alternately, one of ordinary skill could generate the input table for the motor without the aid of software programs. For example, the cam profile for cycloidal motion having dwells of constant velocity comprises a minimum velocity equal to $\omega_{min}$, a change in velocity, $\Delta\omega$, equal to $\omega_{max}-\omega_{min}$, and a rise time $\beta$ of the motion equal to $\tau_{TRANS}/2$. The resulting function of angular position is as follows:

$\theta_{act} = \omega_{min}*t$ when $0 \le$ time in cycle, $t \le \tau_R$ $\theta_{act} = \omega_{min}*t + \frac{1}{2}*\Delta\omega*\beta*((t-\tau_R)/\beta - \sin((t-\tau_R)*\pi/\beta)/\pi)$ when $\tau_R < t < \tau_R + \beta$ $\theta_{act} = \omega_{min}*t + \frac{1}{2}*\Delta\omega*\beta + \omega_{max}*(t-\tau_R-\beta)$ when $\tau_R + \beta \le t \le \tau_R + \beta + \tau_A$ $\theta_{act} = \omega_{min}*t + \frac{1}{2}*\Delta\omega*\beta + \omega_{max}*\tau_A + \frac{1}{2}*\Delta\omega*\beta*((t-\tau_R-\beta-\tau_A)/$ $\beta - \sin((t-\tau_R-\beta-\tau_A)*\pi/\beta)/\pi)$ when $\tau_R+\beta+\tau_A < t \le \tau$ Profiles other than the cycloidal profile can be found in Machinery's Handbook, the 25$^{th}$ Edition.

If a radius is chosen for the transferring device that is not optimum, the transferring device will accomplish the desired changes in velocities, however, the timing for such changes will not correspond to that which is desired. For instance, if the Radius is slightly greater than optimal, using the equations above, the actual distance traveled during the transition is less than needed to position the transferring device 50 at the start of the application zone 23 even though the transferring device 50 achieves the desired angular velocity.

Figure 8A:
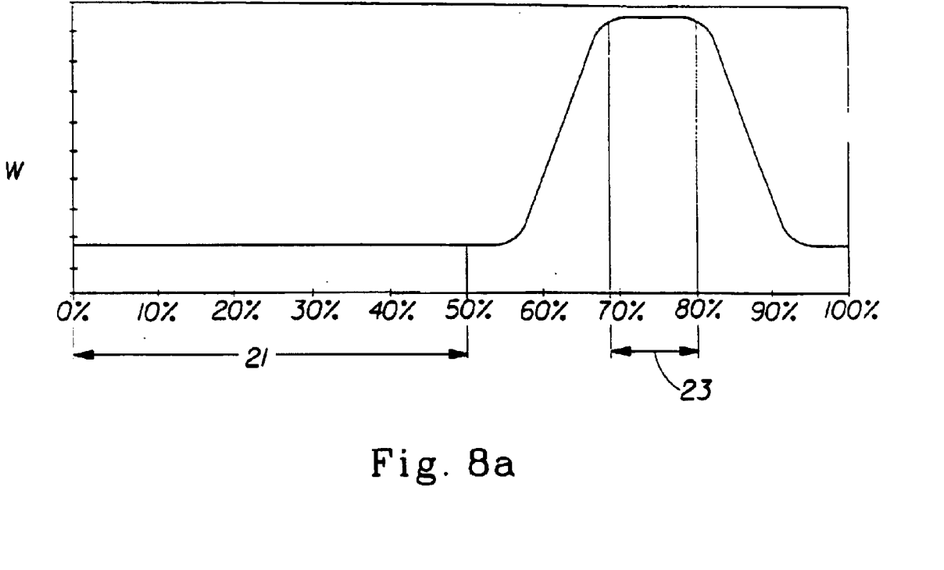
FIG. 8A representatively shows an alternate speed profile for a motor output wherein the rise time P has been decreased to allow for a non-optimal radius without changing the maximum or minimum rotational velocity in the system.
Figure 8B:
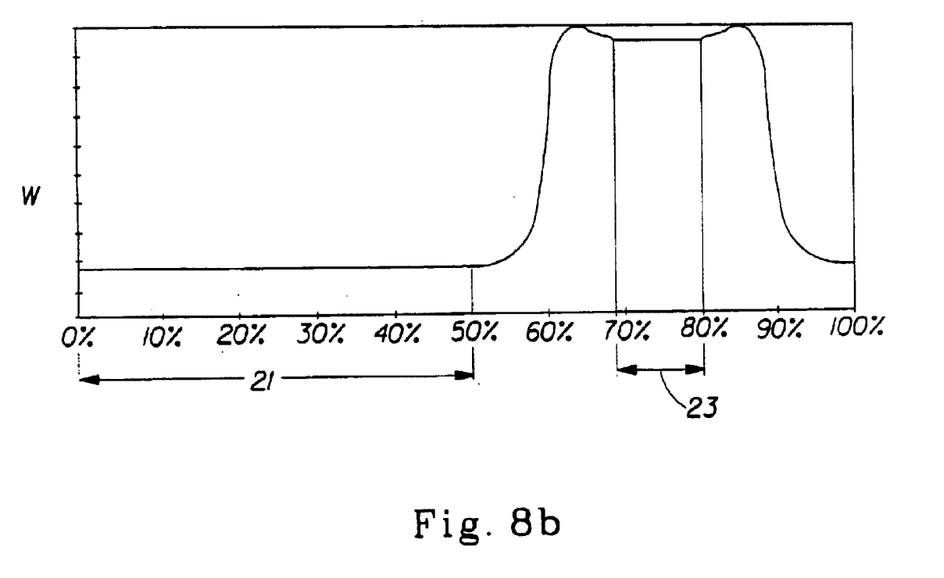
FIG. 8B representatively shows an alternate speed profile for a motor output wherein the maximum rotational velocity during the period of transition from receiving to application zone exceeds the average rotational velocity in the application zone to allow for a non-optimal radius.
Figure 8C:
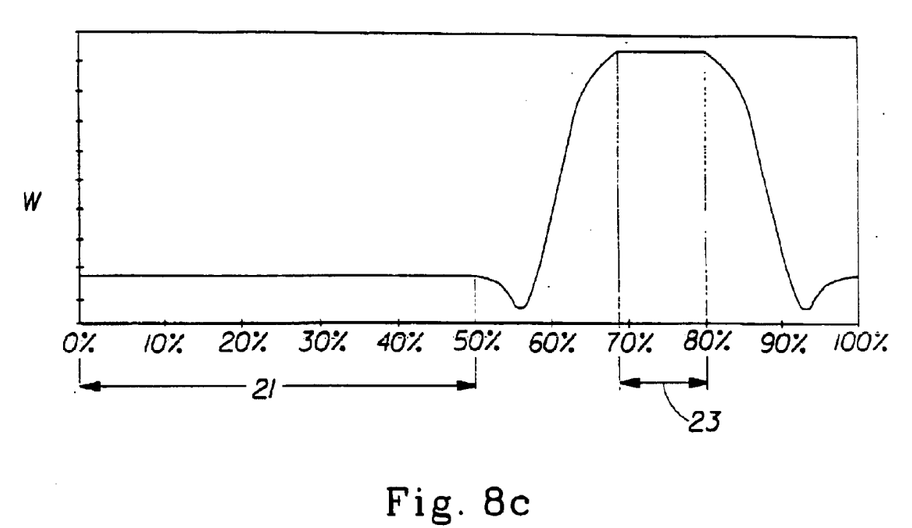
FIG. 8C representatively shows an alternate speed profile for a motor output wherein the minimum rotational velocity during the period of transition from receiving to application zone is less than the average rotational velocity in the receiving zone to allow for a non-optimal radius.

There are three possible ways to achieve speed profiles accommodating pick up and transfer using a non-optimal Radius. First, the rise time P can be decreased by spending more time at $\omega_{min}$ as shown in FIG. 8A. Secondly, as shown in FIG. 8B, the maximum angular velocity in the transition zone can be greater than the $\omega_{max}$ in the application zone 23. Thirdly, the minimum angular velocity in the transition zone can be less than the $\omega_{min}$ in the receiving zone 21 as shown in FIG. 8C.

Using the same cam formulas, one can determine the maximum accelerations generated during the motion using the same family of cam profiles. For example, for the cycloidal profile used above, the peak acceleration is $(\Delta\omega*\pi)/(2*\beta)$. This is important because, for high speed applications, the limiting design factor in the apparatus 20 is motor 64 torque capability at the desired angular velocities. One of ordinary skill in the art can determine total torque requirements for the apparatus 20 for a given application based on the masses and radii of gyration for the different components of the apparatus 20 and the expected accelerations.

As compared to conventional methods for changing the speed of a discrete part so that it can be applied to a continuously moving carrier (such as the slip cut method described above), the use of programmable motors provides the ability to obtain greater changes in speed and to maintain constant speeds for a fixed duration. The fixed speed dwell achieved by programmable motors can be accurately and quickly generated to control the length and placement of the parts. In comparison to the noncircular gear method described above, the use of programmable motors provides the ability to change the profile at will without requiring the fabrication of new parts.

For example, in the various aspects of the invention, the profile generated by the programmable motor 64 is analytically designed such that the rotatable transferring device 50 receives the parts 30 in the receiving zone 21 while maintaining a constant surface speed substantially equal to the speed of the parts 30. Moreover, the output profile of the motor 64 is designed such that the surface speed of the rotatable transferring device 50 changes to a second constant surface speed as the rotatable transferring device 50 moves from the receiving zone 21 to the application zone 23. The term "surface speed," as used herein, refers to the speed of the circumferential, outer peripheral surface of the shell segment 51. The output profile of the motor 64 can be designed such that the speed of the parts 30 being transferred is substantially equal to the speed of the carrier 80 as the parts are applied to the carrier in the application zone 23. The surface speed of the shell segment 50 is maintained substantially constant in the receiving zone 21 and in the application zone 23 from at least about 0 to about 300 degrees of rotation, desirably from about 5 to about 300 degrees of rotation, and more desirably from about 5 to about 240 degrees of rotation of the transferring device 50. In addition, the surface speed increase or decrease of the shell segment 51 as it moves from the receiving zone 21 to the application zone 23 defines a speed ratio of from at least about 100:99 to about 50:1, desirably from about 20:19 to about 25:1, and more desirably from about 10:9 to about 20:1. The term "speed ratio", as used herein, defines the ratio of the surface speed of the shell segment 51 as the parts 30 are applied to the carrier 80 in the application zone 23 to the surface speed of the shell segment 51 as the parts 30 are received in the receiving zone 21.

It has been described above how the required torque and angular speed of the apparatus determine the needed motor capability. For high speed applications common in the manufacture of articles such as diapers, training pants, among other uses, the peak torque requirements of the apparatus 20 combined with the resulting acceleration at the motor 64 will require very high torque to inertia properties in the motor 64. Motors capable of such flux densities are typically of rare earth permanent magnet design or more powerful, and can be purchased from manufacturers of motors such as Rockwell Automation located in Milwaukee, Wis.

In some embodiments it may be necessary to have more than one shell segment per transferring device driven by a single motor, particularly where the process includes secondary operations that are preferably performed at constant speed (see below). It may also be necessary to have multiple shell segments per transferring device in order to increase the radius from the center of rotation to the arcuate outer surface of the shell segments. The radius of a transferring device having a single shell segment may be so small that secondary parts of the design (such as porting airflow for vacuum across the shell segment) may be impractical. Based on the equation above for determining Radius, adding shell segments per transferring device results in an increase in Radius. For example, increasing the number of shell segments per transferring device from one to three triples the Radius.

Additional shell segments also result in an increase in motor torque which is determined from the following expression.

$$T = I_{motor} * \alpha_{motor} + I_{load} * \alpha_{motor} * (N_{driving}/N_{driven})^2$$

where $I_{motor}$—is the moment of inertia of the motor including anything connected directly to the motor shaft.

$\alpha_{motor}$—is the angular acceleration of the motor $N_{driving}/N_{driven}$—the ratio of the number of teeth on the driving gear to the number of teeth on the driven gear.

$I_{load}$—is the moment of inertia of the load (including the transferring device).

The additional shell segments result in an increase in mass moment of inertia of the transferring device, $I_{load}$. Inertia is a direct function of mass and radius of gyration squared. For a transferring device having three shell segments, the mass can be expected to approximately triple and the radius of gyration can be expected to nearly double. Consequently, the moment of inertia of the transferring device can be expected to be at least ten to twelve times the inertia of an equivalent system having a single shell segment. The increase in inertia results in a decrease in the rotational velocity by a factor of three in a system having three shell segments per transferring device, consequently, the gear ratio, $N_{driving}/N_{driven}$ is increased by a factor of three in order to maintain the required motor acceleration. Overall, the resultant torque requirement for the system having three shell segments per transferring device is 11% greater relative to a transferring device having one shell segment per transferring device. Given that motor capability is the key limiting design factor, an increase of 11% in required torque can be significant and can potentially limit the capacity and application of the apparatus.

Figure 9A:
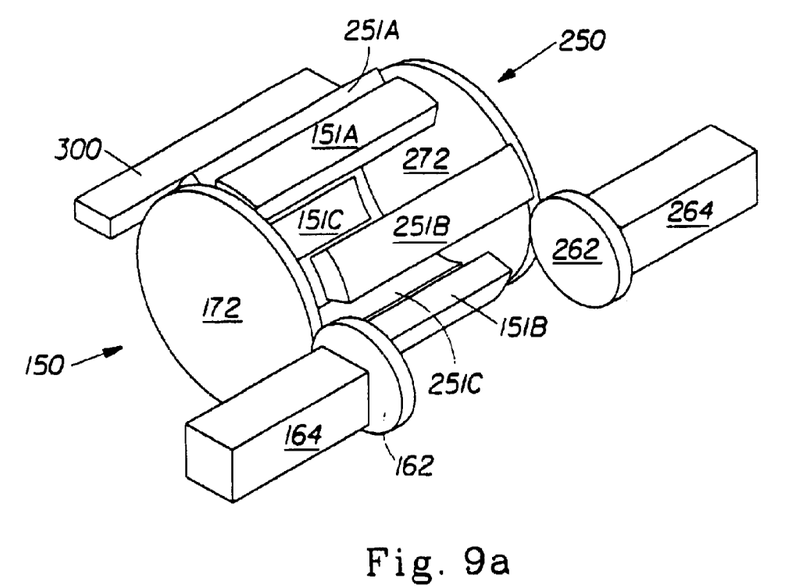
FIG. 9a representatively shows a perspective view of an apparatus according to the present invention including an applicator for accomplishing a secondary process on the parts, and two transferring devices comprising multiple shell segments.
Figure 9B:
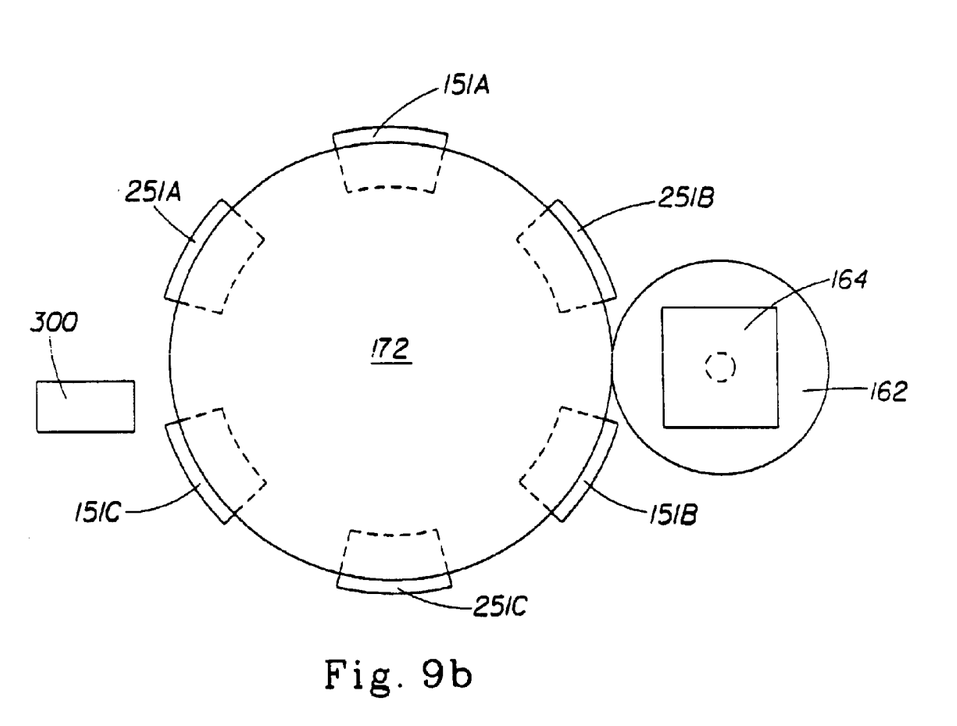

There is no restriction on the number of shell segments per motor besides space and inertial concerns, however, the arrangement pattern of multiple devices is limited. For instance, a transferring device having two shell segments per motor cannot be arranged such that any two shell segments on one transferring device are adjacent to one another in sequence without at least one shell segment from a separate transferring device driven by a separate motor interposed between them. FIGS. 9a and 9b portray an apparatus according to the present invention including an applicator 300 for performing a secondary process on the parts and two transferring devices 150 and 250, each having multiple shell segments. Transferring device 150 comprises three shells 151A, 151B, and 151C and transferring device 250 comprises three shells 251A, 251B, and 251C. Each transferring device is driven by a separate motor 164, 264. As shell segment 151A of transferring device 150 collects a part in the receiving zone 21, the surface speed of shell segments 151A, 151B and 151C are each equal to the receiving speed while the surface speeds of shell segments 251A, 251B, and 251C of transferring device 250 are each equal to either the application speed or some other transitional speed.

Transferring devices comprising two or more shell segments are particularly beneficial where the process includes secondary processes where it is necessary for the part to be moving at a constant speed. As previously described, a secondary process step can be performed on the part such as adhesive application, printing, heating, or moisture application at any point between the receiving zone and the application zone. However, it is preferred to perform the secondary process while the part is moving at constant speed. In applications where the parts are received as a continuous web with no scrap separating the parts during separation, it is preferred that no gaps occur between adjacent shell segments during the transfer in the receiving zone. For instance, where the secondary process involves the application of an adhesive, it is preferred that the parts move at a constant speed during the application with no gaps in between parts so that the metering rate of the adhesive can be constant and not intermittent.

In order to perform a secondary process on the part at a constant speed with no gaps, the secondary process must be performed on the part before the transferring device starts to accelerate. In other words, the time at the receiving speed is lengthened so that the full arc length of the shell segment of the transferring device (assuming that the entire length of the part is required) passes through the process. For example, if the process involves application of an adhesive, then the entire arc length passes underneath the nozzle of the adhesive applicator. This presents a challenge for a transferring device comprising a single shell segment driven by a single motor since the sum of the receiving time, the application time, and the time for the secondary process might exceed the total cycle time. This problem may be resolved by adding a second transferring device having a single shell segment driven by a separate motor or by using a transferring device having more than one shell segment per transferring device.

In an ideal state, as one shell segment finishes receiving a part, the next shell segment in sequence starts receiving a part. Generally, the parts entering the transferring device are part of a continuous web having no spacing in-between at the receiving zone. Consequently in order to have a no gap situation, shell segments in the receiving zone should have no gap between them. However, in reality, variability in motor positioning, head dimensions, gear backlash, etc. can cause the position of the transfer device to have some variability in rotational position resulting in gaps or even forcible contact therebetween. Since it is not desired to have two transfer devices contact forcibly, there are a few choices that can be made.

Figure 10:
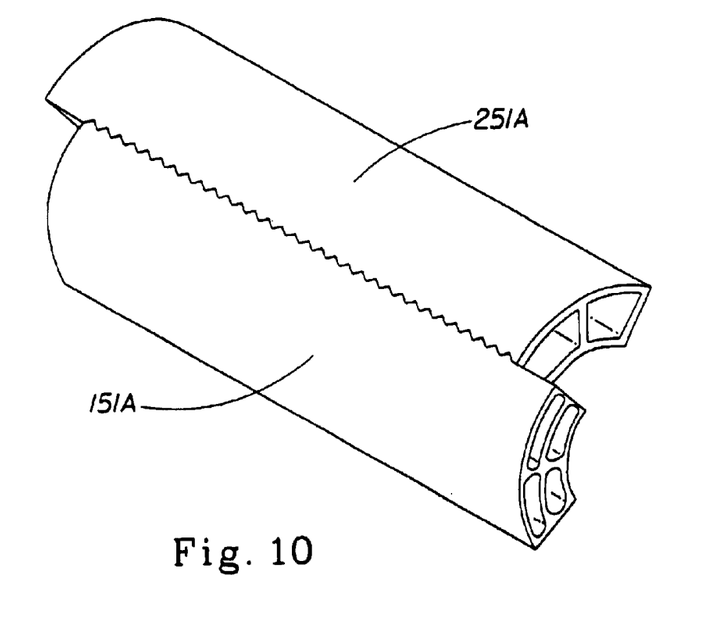
FIG. 10 representatively shows an isometric view of adjacent shell segments according to the present invention having grooved leading and trailing edges that mesh.

First, the shell segments can be fabricated to be a little shorter in arc length than the part to be received, and then the devices can be brought close but not contacting each other. This avoids contact, but does not allow for complete control of the lead and trail edges of the part. This may or may not impact product quality, depending on the part properties. Second, the shell segments can have a shock-absorbing structure on the lead and/or trail edges, so that contact does not generate damage. Depending on the desired cycle life of the transfer device, this might be as simple as placing a compressible foam or as complex as a spring-loaded wall. Third, the shell segments can have mating surfaces which allow the devices to coexist radially and tangentially but not axially. As shown in FIG. 10, shell segments 151A and 251A can have grooved or otherwise modified leading and trailing edges that mesh with similarly modified edges on adjacent shell segments.

What is claimed is:

1. An apparatus for forming parts from a continuously moving web of parts material, receiving the parts traveling at a first speed in a receiving zone, and applying the parts onto a carrier traveling at a second speed through an application zone, the apparatus comprising:
   a rotatable knife roll for severing the continuously moving web of parts material to form the parts;
   an independent knife roll driving mechanism for rotating the knife roll, the independent knife roll driving mechanism including a programmable motor coupled to the knife roll via a transmitting mechanism for conveying energy therebetween;
   at least two rotatable transferring devices for receiving the parts in the receiving zone and applying the parts in the application zone; and
   at least two independent transferring device driving mechanisms for rotating the transferring devices, the independent transferring device driving mechanisms including programmable motors coupled to the transferring devices via transmitting mechanisms for conveying energy therebetween;
   wherein the independent transferring device driving mechanisms maintain the transferring devices at first surface speeds in the receiving zone as the transferring devices pick up the parts and maintain the transferring devices at second surface speeds in the application zone as the transferring devices apply the parts onto the carrier.

2. The apparatus of claim 1 further comprising a knife anvil roll having a surface speed substantially equal to a velocity of the web of parts material.

3. The apparatus of claim 1 wherein the independent knife roll driving mechanism maintains the knife roll at a cutting surface speed substantially equal to a velocity of the web of parts material while each of the parts is being severed from the web of parts material and at a different cutting surface speed during intervals between parts being severed from the web of parts material.

4. The apparatus of claim 1 wherein the first surface speeds of the transferring devices are substantially equal to the first speed of the parts in the receiving zone and the second surface speeds of the transferring devices are substantially equal to the second speed of the carrier in the application zone.

5. The apparatus of claim 1 wherein each of the transferring devices comprises at least one shell segment having an arcuate outer surface, each shell segment moves along an orbital path that passes through the receiving zone during rotation of the transferring devices, and each shell segment receives the parts in the receiving zone and hold the parts against the arcuate outer surface utilizing a vacuum, an electrostatic force, or a coefficient of friction before applying the parts onto the carrier in the application zone.

6. The apparatus of claim 1 wherein the carrier is a carrier web having adhesive for holding the parts after the parts are applied onto the carrier web.

7. The apparatus of claim 6 further comprising an opposing roll for compressing the parts and the carrier web between the transferring devices and the opposing roll while the parts are applied onto the carrier web.

8. An apparatus for forming parts from a continuously moving web of parts material, receiving the parts traveling at a first speed in a receiving zone, and applying the parts onto a carrier web traveling at a second speed through an application zone, the apparatus comprising:
   a rotatable knife roll for severing a continuously moving web of material to form the parts;
   an independent knife roll driving mechanism for rotating the knife roll, the independent knife roll driving mechanism including a programmable motor coupled to the knife roll via a transmitting mechanism for conveying energy therebetween;
   a bonding anvil roll rotating at a surface speed substantially equal to a velocity of the carrier web;
   at least two rotatable transferring devices for receiving the parts in the receiving zone and transferring the parts onto the bonding anvil roll;
   at least two independent transferring device driving mechanisms for rotating the transferring devices, the independent transferring device driving mechanisms including programmable motors coupled to the transferring devices via transmitting mechanisms for conveying energy therebetween; and
   a bonding pattern roll rotating at a surface speed substantially equal to a velocity of the carrier web;
   wherein the independent transferring device driving mechanisms maintain the transferring devices at first surface speeds in the receiving zone as the transferring devices pick up the parts and maintain the transferring devices at second surface speeds as the transferring devices transfer the parts to the bonding anvil roll; and
   wherein the bonding anvil roll applies the parts to the carrier web and compresses the parts and the carrier web between the bonding anvil roll and the bonding pattern roll, thereby bonding the parts to the carrier web.

9. The apparatus of claim 8 wherein the independent knife roll driving mechanism maintains the knife roll at a cutting speed substantially equal to a velocity of the web of parts material while each of the parts is being severed from the web of parts material and at a different cutting surface speed during intervals between parts being severed from the web of parts material.

10. The apparatus of claim 8 wherein the first surface speeds of the transferring devices are substantially equal to the first speed of the parts in the receiving zone and the second surface speeds of the transferring devices are substantially equal to the second speed of the carrier web while the transferring devices transfer the parts to the bonding anvil roll.

11. The apparatus of claim 8 wherein each of the transferring devices comprises at least one shell segment having an arcuate outer surface, each shell segment moves along an orbital path that passes through the receiving zone during rotation of the transferring devices, and each shell segment receives the parts in the receiving zone and hold the parts against the arcuate outer surface utilizing a vacuum, an electrostatic force, or a coefficient of friction before transferring the parts onto the bonding anvil roll.

12. The apparatus of claim 8 wherein the carrier web has adhesive for holding the parts after the parts are applied onto the carrier web.

13. The apparatus of claim 8 wherein the knife roll is a die roll.

14. A method for forming parts from a continuously moving web of parts material, receiving the parts traveling at a first speed in a receiving zone, and applying the parts to a carrier traveling at a second speed through an application zone, the method comprising the steps of:
providing a rotatable knife roll;
providing an independent knife roll driving mechanism for rotating the knife roll, the independent knife roll driving mechanism including a programmable motor coupled to the knife roll via a transmitting mechanism for conveying energy therebetween;
rotating the knife roll to sever the continuously moving web of parts material to form the parts;
providing at least two rotatable transferring devices;
providing at least two independent driving mechanisms for rotating the transferring devices, the independent driving mechanisms including programmable motors coupled to the transferring devices via transmitting mechanisms for conveying energy therebetween;
programming the programmable motors coupled to the transferring devices to rotate the transferring devices through the receiving zone at first surface speeds and to rotate the transferring devices through the application zone at second surface speeds; and
rotating the transferring devices through the receiving zone to receive the parts and through the application zone to apply the parts to the carrier.

15. The method of claim 14 wherein the step of rotating the knife roll includes rotating the knife roll at a cutting surface speed substantially equal to a velocity of the web of parts material while each of the parts is being severed from the web of parts material and at a different cutting surface speed during intervals between parts being severed from the web of parts material.

16. The method of claim 14 further comprising the steps of providing an opposing roll and compressing the parts and the carrier web between the transferring devices and the opposing roll while the parts are applied onto the carrier web.

17. The method of claim 14 wherein the carrier is a carrier web having adhesive for holding the parts after the parts are applied onto the carrier web.

18. A method for forming parts from a continuously moving web of parts material, receiving the parts traveling at a first speed in a receiving zone, and applying the parts onto a carrier web traveling at a second speed through an application zone, the method comprising the steps of:
providing a rotatable knife roll;
providing an independent knife roll driving mechanism for rotating the knife roll, the independent knife roll driving mechanism including a programmable motor coupled to the knife roll via a transmitting mechanism for conveying energy therebetween;
rotating the knife roll to sever the continuously moving web of parts material to form the parts;
providing a bonding anvil roll rotating at a surface speed substantially equal to a velocity of the carrier web;
providing at least two rotatable transferring devices;
providing at least two independent transferring device driving mechanisms for rotating the transferring devices, the independent transferring device driving mechanisms including programmable motors coupled to the transferring devices via transmitting mechanisms for conveying energy therebetween;
programming the programmable motors coupled to the transferring devices to rotate the transferring devices at first surface speeds in the receiving zone as the transferring devices pick up the parts and to rotate the transferring devices at second surface speeds as the transferring devices transfer the parts to the bonding anvil roll;
rotating the transferring devices to receive the parts in the receiving zone and to transfer the parts onto the bonding anvil roll;
applying the parts from the bonding anvil roll onto the carrier web;
providing a bonding pattern roll rotating at a surface speed substantially equal to a velocity of the carrier web; and
compressing the parts and the carrier web between the bonding anvil roll and the bonding pattern roll, thereby bonding the parts to the carrier web.

19. The method of claim 18 wherein the step of rotating the knife roll includes rotating the knife roll at a cutting speed substantially equal to a velocity of the web of parts material while each of the parts is being severed from the web of parts material and at a different cutting surface speed during intervals between parts being severed from the web of parts material.

20. A method for receiving parts traveling at a first speed and applying the parts to a carrier traveling at a second speed comprising the steps of:
providing at least two rotatable transferring devices;
providing at least two independent driving mechanisms for rotating the transferring devices, the independent driving mechanisms including programmable motors coupled to the transferring devices;
programming the programmable motors to rotate the transferring devices through a receiving zone at first surface speeds to receive the parts and to rotate the transferring devices through an application zone at second surface speeds to apply the parts to the carrier;
wherein the first surface speed is greater than the second surface speed.

* * * * *

UNITED STATES PATENT AND TRADEMARK OFFICE
CERTIFICATE OF CORRECTION

PATENT NO. : 6,814,217 B2  Page 1 of 1
DATED : November 9, 2004
INVENTOR(S) : Blumenthal et al.

It is certified that error appears in the above-identified patent and that said Letters Patent is hereby corrected as shown below:

Column 3,
Line 52, delete "P" and insert -- $\beta$ --.

Column 9,
Line 48, delete "(4*$n$)" and insert -- (4*$\pi$) --.

Column 10,
Line 33, delete "P" and insert -- $\beta$ --.

Signed and Sealed this

Twenty-seventh Day of December, 2005

JON W. DUDAS
*Director of the United States Patent and Trademark Office*